United States Patent [19]

Jacobs

[11] 4,173,505
[45] Nov. 6, 1979

[54] METHOD OF MAKING A DISPOSABLE DENTAL TRAY OR THE LIKE BY COMBINING DISSIMILAR FOAMS

[75] Inventor: I. Murray Jacobs, Birmingham, Mich.

[73] Assignee: Sybron Corporation, Rochester, N.Y.

[21] Appl. No.: 874,850

[22] Filed: Feb. 3, 1978

[51] Int. Cl.² .......................................... B29C 17/03
[52] U.S. Cl. .................................... 156/285; 433/89; 128/136; 264/46.8
[58] Field of Search ................ 156/285, 245, 224; 264/321, 322, 45.1, 46.8; 32/1, 14 B; 428/304, 305, 331, 315, 423, 424, 425; 128/136; 53/22 A, 26, 28, 29, 30 R, 40

[56] References Cited
U.S. PATENT DOCUMENTS

| | | | |
|---|---|---|---|
| 3,148,103 | 9/1964 | Gallagher | 156/224 |
| 3,577,700 | 5/1971 | Bippus et al. | 53/30 |
| 3,589,592 | 6/1971 | Tigner | 264/46.8 |
| 3,657,044 | 4/1972 | Singer | 156/285 |
| 3,954,537 | 5/1976 | Alfter et al. | 264/46.8 |

FOREIGN PATENT DOCUMENTS 50-25879  8/1975  Japan ................................. 53/30 R Primary Examiner—Caleb Weston
Attorney, Agent, or Firm—Theodore B. Roessel; Roger Aceto

[57] ABSTRACT

Disclosed is a method of manufacturing a laminated plastic article such as a dental tray or the like having a hydrophilic foam formed and heat bonded to a polyethylene foam substrate. The dental tray has upper and lower portions hinged together, and contoured to properly accommodate the particular tooth structure of the posterior and anterior teeth and the general geometry of the upper and lower jaws. In a vacuum forming operation a laminated sheet is formed, the tray is appropriately contoured and the tray cut or blanked from the sheet.

5 Claims, 6 Drawing Figures

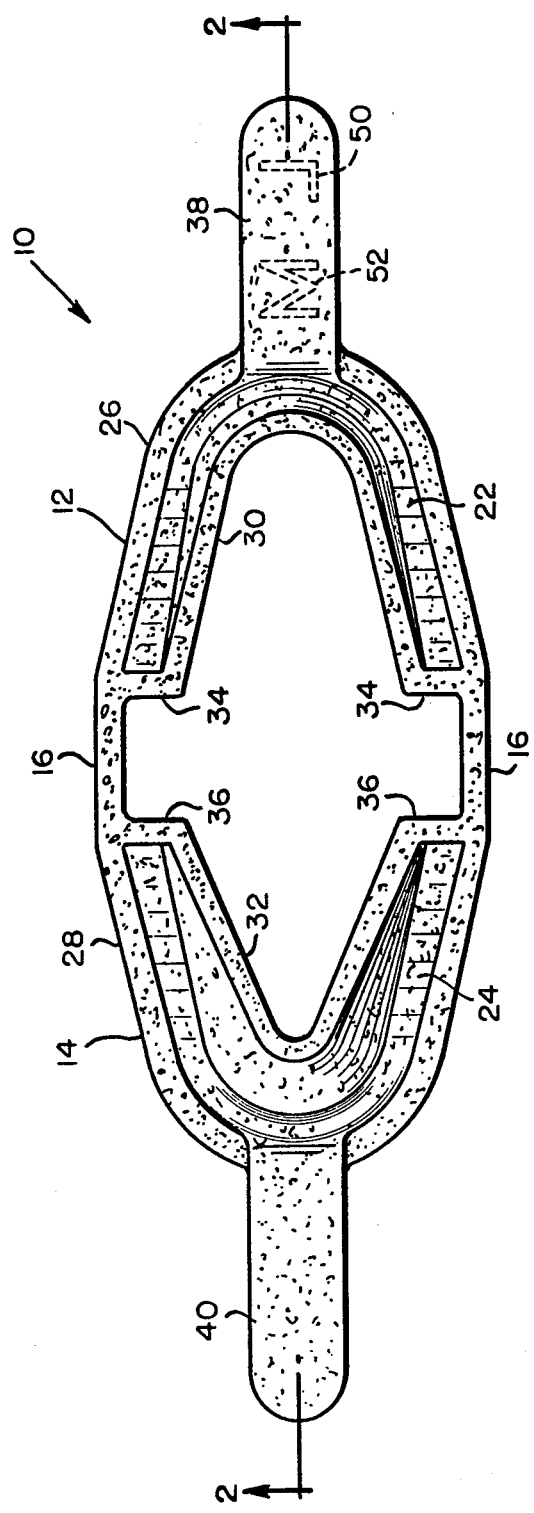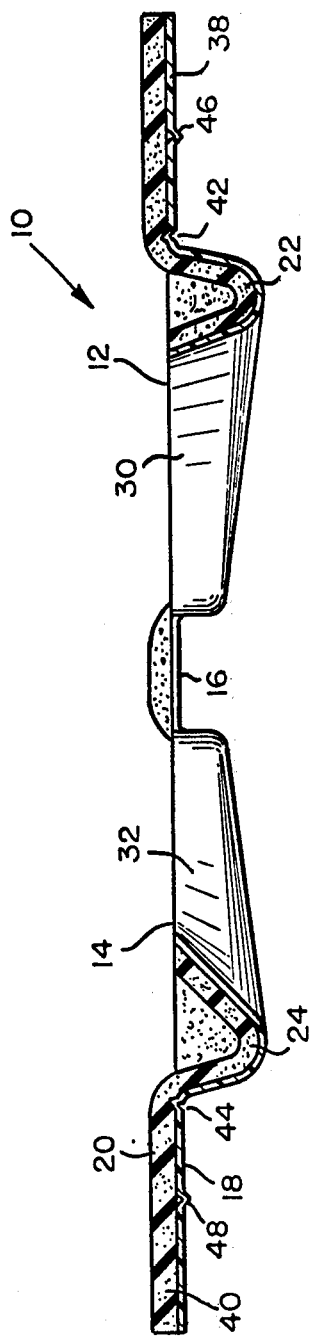

METHOD OF MAKING A DISPOSABLE DENTAL TRAY OR THE LIKE BY COMBINING DISSIMILAR FOAMS

SUMMARY OF THE INVENTION

The present invention relates generally to a disposable dental tray used in the application of medicaments such as fluoride and the like to the teeth. More particularly, the invention relates to a dental tray having hinged together upper and lower portions so that both the upper and lower teeth can be treated simultaneously, the portions being manufactured together as a unit. The geometry of the upper and lower tray portions allows proper accommodation of the tooth structure of the posterior and anterior teeth, one of the trays being specifically designed for the upper dental arch and the other for the lower.

Dental trays used in fluoride applications are well known in the art. One such tray, for example, being disclosed in U.S. Pat. No. 3,536,069. The current practice in dentistry for the application of fluoride to teeth employs a reusable tray and a disposable insert. The insert is made of a sponge-like material and serves both as a carrier and applicator for the fluoride gel or liquid to be applied to the teeth. In this respect, the insert is first placed within the tray and then the fluoride gel or liquid added. The tray is then placed into the mouth and when the user bites down, the sponge-like material of the insert forces the fluoride material around the teeth. After use, the insert is removed from the tray and discarded. The tray, itself, may be reused.

Trays which are disposable such as shown in U.S. Pat. Nos. 3,955,281 and 3,527,219 are also available but these are usually single trays, that is either upper or lower. Some of these disposable trays also require a separate foam insert, while others do not use any insert. Trays not employing a foam or sponge-like insert are generally less effective in applying the fluoride.

In the present invention, tray portions specifically designed to conform to the geometry of the upper and lower dental arches are hinged together. Each tray portion includes a soft hydrophilic foam insert formed and bonded to a soft polyethylene foam substrate. The bonding preferably is by heat sealing to form a laminated tray structure. Trays formed in this manner are low cost and cannot be heat sterilized, so they are completely disposable after use.

DESCRIPTION OF THE DRAWINGS

FIG. 1 is a plan view of the disposable dental tray of the present invention;

FIG. 2 is a view taken along lines 2—2 of FIG. 1;

DESCRIPTION OF THE PREFERRED EMBODIMENTS

Figure 3:
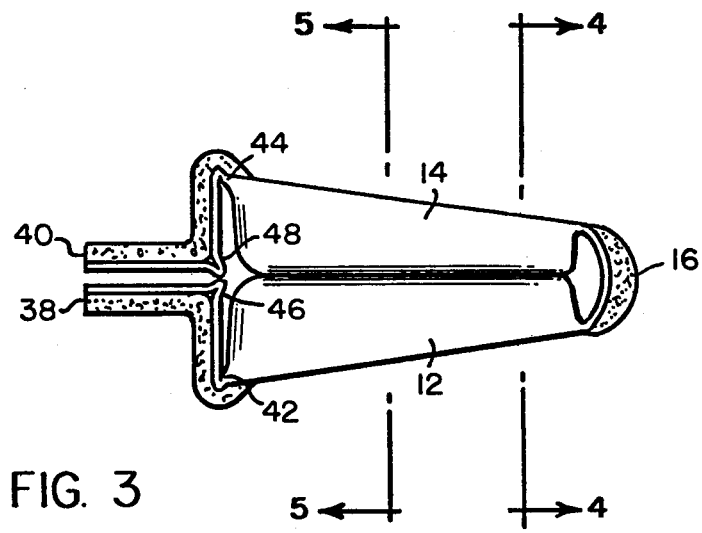
FIG. 3 is a side elevation view of the tray disposed for use.

Referring to the drawings, FIG. 1 shows the dental tray of the present invention, generally indicated at 10, to include two U-shaped portions, a lower portion 12 for treating the lower dentition and an upper portion 14 for treating the upper dentition. The two portions are connected adjacent their posterior ends by a bridging strap 16 which forms a hinge when the tray is in use. As best shown in FIG. 2, each tray portion consists of an outer shell or substrate 18, preferably made in a single piece by vacuum forming from a soft polyethylene foam. Bonded to the interior of the shell is a soft hydrophilic foam lining 20. The bonding can be accomplished by any suitable means such as with a chemical bonding agent. However, it is preferred that the hydrophilic foam layer 20 be heat bonded to substrate 18 so as to eliminate any harmful effects from migrating chemicals or leaching of bonding agents.

While the entire tray of the present invention is formed in one integral piece, the various components of each tray portion will be described herein as separate elements to simplify the description thereof. It should also be understood that these separately described elements each include the outer polyethylene foam shell or substrate 18 bonded, preferably by heat bonding, to the hydrophilic foam lining 20 so as to form a laminated structure.

Figure 4:
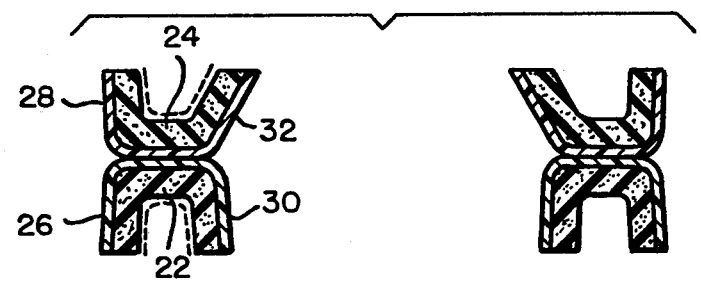
FIG. 4 is a view taken along lines 4—4 of FIG. 3.
Figure 5:
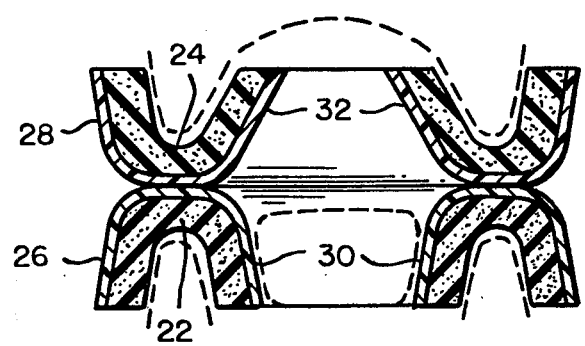
FIG. 5 is a view taken along lines 5—5 of FIG. 3.

Both the lower and upper tray portions each have a base 22, 24 respectively which in plan view (FIG. 1) is generally U-shaped to approximate the curve of the dental arch. Each base adjacent the posterior end is substantially flat (FIG. 4) to accommodate the relatively flat molars shown in dotted line which are found at this portion of the dental arch. As shown in FIGS. 2 and 5, the base of each tray then becomes convex from the bicuspid area to the anterior area to better accommodate the bicuspid, canine and incisors found in the anterior portion of the dental arch. In addition, each base 22, 24 is oriented in a plane inclined with respect to the horizontal (FIG. 2), with the posterior ends being higher than the anterior. This allows the trays to properly accommodate the short teeth found generally in the posterior region and the longer canine and incisors found in the anterior portion.

Upstanding from the inner and outer peripheries of each base 22, 24 are buccal walls 26, 28 and lingual walls 30, 32 respectively. The posterior ends of each base also have upstanding rear walls 34 and 36 so that both the lower and upper tray portions 12, 14 are closed troughs. The strap 16 which connects the upper and lower tray portions extend between rear walls 34 and 36 adjacent the buccal walls of each tray (FIG. 1). The purpose of this is to locate the strap as far as possible away from the patient's tongue. This decreases the likelihood that the strap will contact the rear sides of the tongue when in use and cause the patient to gag.

As shown in FIGS. 2 and 3 the buccal and lingual walls are higher at the anterior end than at the posterior ends of each tray portion. In this manner, the troughs formed by the base and upstanding walls of each tray gradually increase in depth from the posterior ends to the anterior end. From FIG. 4, it is seen that the buccal walls 26, 28 and lingual walls 30, 32 of the lower and upper tray portions extend generally normal to bases 22, 24, adjacent the posterior ends of the tray portions. This provides the posterior ends of the tray portions with a generally square cross section so as to better accommodate the generally low, flat configuration of the molars found in this area. The buccal wall of each tray portion continues to extend generally normal to the tray base around the bicuspid area and toward the anterior portion as shown in FIGS. 5 and 2 respectively.

The lingual walls 30, 32 of each tray which are substantially normal to each base adjacent the posterior ends, gradually become inclined with respect to the bases so that at the anterior they upstand from the bases at an angle inclined away from their respective buccal walls. As shown in FIG. 2, lingual walls 30, 32 reach a maximum inclination at the anterior end with the inclination of the upper lingual wall 32 away from buccal wall 28 being greater than that of the lower lingual wall 30 from buccal wall 26.

Inclining the lingual walls in this fashion permits the dental tray of the present invention to better fit the geometry of the inter-oral cavity. For example, the larger inclination of the upper lingual wall 32 which reaches a preferred maximum of 45° allows it to fit the upper oral cavity in contact with the palate as shown in dotted line in FIG. 5. The inclination of the lower lingual wall 30 reaches a preferred maximum of 15° which allows it to fit the lower oral cavity and provide clearance for free movement of the tongue as shown in dotted line in FIG. 5.

Both the lower and upper tray portions 12, 14 are provided with handles 38, 40 respectively. Each handle is formed integral with and extends outwardly from the top of the buccal walls 26, 28. The connection of each handle to the buccal wall is sufficiently flexible so as to form a hinge at the connection.

As shown in FIG. 2, it is preferred that the substrate 18 of each handle be provided with a score line 42, 44 respectively on its bottom surface to facilitate bending along the line of attachment to the buccal wall. Each handle has an additional score line 46, 48 on the upper surface of the substrate forward of the buccal wall to provide a second hinge.

Then when trays 12 and 14 are bent to the in-use position shown in FIG. 3, the score lines 42, 44, 46 and 48 allow the handles to be pinched together and held between the thumb and index finger of the user without straining or outwardly distorting the buccal anterior wall.

If desired, appropriate indicia such as that shown by reference 50 can be provided on the substrate of one or both handles 38, 40 to identify the lower and upper trays. Other indicia such as that shown at 52 can be provided on either of the handles to indicate the size of the tray as for example "S" for small, "M" for medium and "L" for large.

The substrate 18 is preferably made of a closed cell polyethylene foam which is not cross linked and non-absorbent. This polyethylene can be purchased in sheet form with skin on both sides and a density of 3½ to 6 pounds per cubic foot. The density can be selected depending upon the rigidity desired of the substrate. The melting temperature of this polyethylene as about 225° F.

The inner hydrophilic foam 18 is preferably an open cell polyurethane foam 5/32 to ¼ inches thick with a density of about 1.3 to 2.3 pounds per cubic foot and a melting temperature of about 240°-260° F. While a polyurethane foam in either the polyether or polyester form may be used, the polyether is preferred because it is the more hydrophilic. A hydrophilic foam such as that described is used for the inner foam layer 20 because the aqueous properties of the flouride gel used in the treatment as well as any saliva entering the tray will cause the hydrophilic foam to swell. This swelling in turn, causes the foam to embrace the teeth and forces the fluoride gel into close intimate contact with the teeth and into the proximal areas between the teeth.

In use, the appropriate medicament such as a fluoride gel is first introduced into each tray portion and absorbed by the hydrophilic foam inner lining 20. The upper and lower tray portions are then folded about strap 16 and handles 38, 40 squeezed together between the thumb and index finger which brings the tray portions and handles to the position shown in FIG. 3. Since the handles are flexible, they bend easily at the score lines 42, 44, 46 and 48 so the buccal walls are not pulled out of position or deformed. In this position, the straps 16 are in tension which produces a spring-like tension tending to force the upper and lower tray portions apart and against the teeth. Since these hinges in the tray in-use position are located vertically to the trays and are spaced from the patient's tongue, they do not protrude into the rear cavity of the mouth or contact the tongue, thereby avoiding patient discomfort.

The dental tray is then inserted into the patient's mouth. The tray is designed to be flexible so that if needed, the posterior ends can be squeezed together to narrow the U-shape and facilitate placement into the patient's mouth. The patient then bites down on the tray to effect the treatment.

Figure 6:
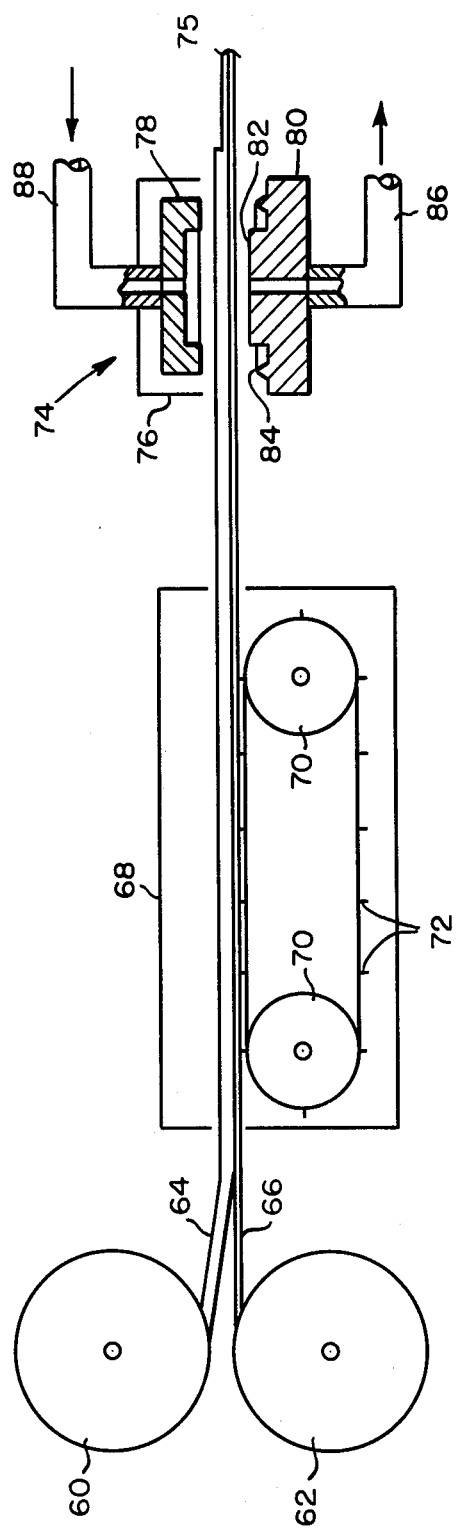
FIG. 6 is a schematic diagram showing the manufacturing steps.

FIG. 6 illustrates schematically, the preferred method steps of manufacturing the dental tray. In this respect, the polyethylene and polyurethane materials of the dental tray are provided in sheet form, preferably on rollers 60 and 62 respectively. The polyethylene and polyurethane foam sheets 64, 66 are unrolled and continuously fed into and through an oven or other suitable heating chamber 68. The sheets are oriented so that the polyethylene sheet 64 is supported on and carried by the polyurethane sheet 66. Within the oven there is an endless chain drive mechanism 70. The links of the chain are provided with upstanding needle-like members 72. These members 72 grip and carry the polyurethane sheet 66 and therefore the polyethylene sheet 64 through heating chamber 68. In the method as practiced, chamber 68 is approximately 10–12 feet long and is heated by infra red heaters to about 700°–900° F. The chain drive moves the sheets through the chamber at about 40 feet per minute so that any point on either sheet is heated for only 15 to 18 seconds. As this feed rate, it has been found that even though the chamber temperature is significantly higher than the melting temperature of the sheets 64, 66 they do not remain within the chamber long enough to completely melt. It is believed that what does occur under these conditions is a flash heating of surfaces of sheets 64, 66 to a point between the melting point of the polyethylene and polyurethane, that is between about 225° F. and 240° F. This softens or partially melts the surface of the polyethylene sheet and makes the surface of the polyurethane sheet tacky. When sheets 64 and 66 leave the heating chamber they are still not joined together.

As the sheets leave the heating chamber they are fed into a vacuum forming mold generally indicated at 74. In the mold, the polyethylene is compressed against the polyurethane to form the laminated sheet indicated at 75. During the forming process, the polyethylene which forms the substrate 18 of the dental tray is compressed. Since it is softened by the previous heating step, it takes the set which accounts for the laminated sheet 75 in FIG. 6 being thinner than the two sheets 64, 66 going into the vacuum form mold. The polyurethane sheet is also compressed in the mold but this material does not take the set and rebounds to its original thickness.

The mold itself includes a clamping ring 76, an upper assist 78 and a lower draw mold 80. A raised die 82 on draw mold 80 represents the male form over which the sheets 64, 66 are drawn to form the dental tray. A knife edge 84 is provided on the draw mold to blank or cut each dental tray from the laminated sheet 75 as it is vacuum formed over the raised die 82.

The operation of vacuum mold 74 is conventional. Clamping ring 76 first closes against lower draw mold 80 to form an air tight seal. Assist 78 then moves into engagement with the lower draw mold. Air is evacuated through line 86 which draws the portions of sheets 64 and 66 within the mold over the raised die 82 to form the dental tray. If desired, a positive pressure can be applied through line 88 to assist the forming process by pushing the sheets 64, 66 down over the raised die 82.

The vacuum forming process draws and compresses the polyethylene sheet 64 against the polyurethane sheet 66 so that the open cell structure of the polyurethane becomes embedded in and bonded to the softened surface of the closed cell polyethylene. This forms the laminated structure of the dental tray wherein the hydrophilic polyurethane foam 20 is heat bonded to the polyethylene substrate 18.

In order to vacuum for the dental tray as described herein, it is important that the two sheets 64, 66 be oriented so as to put the open cell polyurethane foam sheet 66 between the closed cell polyethylene foam sheet 64 and the area of reduced pressure. This allows the differential pressure to move the polyethylene sheet (which has skin on both sides) against the open cell polyurethane. Reversing the orientation would result in the differential pressure moving the polyethylene sheet away from the polyurethane and prevent or at least substantially reduce any bonding between the two sheets.

As set forth hereinabove the present invention also provides for the cutting or blanking or the formed dental tray from laminated sheet 75 simultaneously with the vacuum forming of the tray. This is accomplished by a knife edge 84 which is disposed about the raised die 82 and in plan view (not shown) follows the contours of the dental tray as shown in FIG. 1.

Thus it should be appreciated that the present invention provides a low cost, disposable dental tray which fits closely to the contours of the upper and lower oral cavities and properly accommodates both the posterior and anterior tooth configurations. The method of making the laminated structure by heat bonding together the foamed polyethylene and polyurethane sheets to form respectively the shell and inner hydrophilic foam lining of the tray, provides a dental tray having all the essential components in a single, integral structure.

Having described the invention in detail, what is claimed as new is:

1. A method of making a vacuum formed article having a laminated structure of dissimilar plastic foams comprising the steps of:
    (a) superimposing a sheet of closed cell polyethylene foam on a sheet of an open cell hydrophilic polyurethane foam so that said polyethylene foam sheet is supported on and carried by said polyurethane foam sheet;
    (b) heating said superimposed sheets by conveying the same through a heating chamber which has been heated to a temperature above the melting point of said polyurethane foam sheet, said sheets being passed through said heating chamber at a rate which allows retention of said sheets in said chamber only for a time sufficient to soften the surfaces of said polyethylene sheet and render the surfaces of said polyurethane sheet tacky, said heating step alone being insufficient to result in the bonding of said sheets so that at the end of said heating step said polyethylene sheet and polyurethane sheet remain unjoined with said polyethylene sheet resting and being carried on said polyurethane sheet;
    (c) passing said superimposed sheets from said heating chamber and into a vacuum forming mold; and
    (d) establishing a differential pressure across said superimposed sheets in said mold, said polyethylene sheet being oriented between said sheet of hydrophilic polyurethane foam and the higher pressure for moving and compressing said polyethylene sheet towards and against said sheet of hydrophilic polyurethane foam responsive to said differential pressure for simultaneously bonding said sheets together by embedding the open cell surface of said polyurethane foam sheet in the softened surface of said closed cell polyethylene sheet thereby forming said laminated structure, and vacuum forming the contours of said article.

2. A method as in claim 1 wherein said hydrophilic polyurethane foam is in the polyether form.

3. A method as in claim 1 wherein said differential pressure is created by evacuating from the vacuum form mold adjacent said polyurethane sheet and applying a positive pressure to said vacuum form mold adjacent said polyethylene sheet.

4. A method as in claim 1 including the step of blanking said article from said laminated sheet simultaneously with the vacuum forming of said article.

5. A method as in claim 1, wherein said heating chamber is held at a temperature of about 700°–900° F., said heating chamber being about 10–12 feet long and said superimposed sheets being conveyed through said heating chamber at a rate of about 40 feet per minute.

* * * * *